(12) United States Patent
Glas (10) Patent No.: US 11,954,859 B2
(45) Date of Patent: Apr. 9, 2024

(54) METHODS OF ASSESSING DISEASES USING IMAGE CLASSIFIERS

(71) Applicant: Agendia NV, Amsterdam (NL)

(72) Inventor: Annuska Maria Glas, Assendelft (NL)

(73) Assignee: Agendia NV, Amsterdam (NL)

( * ) Notice: Subject to any disclaimer, the term of this patent is extended or adjusted under 35 U.S.C. 154(b) by 411 days.

(21) Appl. No.: 17/395,169

(22) Filed: Aug. 5, 2021

(65) Prior Publication Data
US 2022/0148178 A1 May 12, 2022

Related U.S. Application Data

(60) Provisional application No. 63/112,623, filed on Nov. 11, 2020.

(51) Int. Cl.
*G06N 20/20* (2019.01)
*G06N 3/08* (2023.01)
(Continued)

(52) U.S. Cl.
CPC .............. *G06T 7/0014* (2013.01); *G06N 3/08* (2013.01); *G06N 20/20* (2019.01); *G06T 7/11* (2017.01);
(Continued)

(58) Field of Classification Search
CPC ...................... G06T 7/0014; G06T 7/11; G06T 2207/10056; G06T 2207/20081; G06T 2207/20084; G06T 2207/30024; G06T 2207/30096; G06N 3/08; G06N 20/20; G16B 40/00; G16H 10/40; G16H 50/20;
(Continued)

(56) References Cited

U.S. PATENT DOCUMENTS

| 2010/0151463 A1 | 6/2010 | Baehner et al. |
| 2010/0247580 A1 | 9/2010 | Coche |

(Continued)

FOREIGN PATENT DOCUMENTS

| EP | 3385392 A1 | 10/2018 |
| WO | 2012/106718 A2 | 8/2012 |

(Continued)

OTHER PUBLICATIONS

Sun et al., A Multimodal Deep Neural Network for Human Breast Cancer Prognosis Prediction by Integrating Multi-Dimensional Data, May/Jun. 2019, IEEE/Acm Transactions On Computational Biology and Bioinformatics, vol. 16, No. 3, (Year: 2019).*

(Continued)

*Primary Examiner* — Said M Elnoubi
(74) *Attorney, Agent, or Firm* — Withers Bergman LLP; Thomas C. Meyers (57) ABSTRACT

The present disclosure provides methods and systems using machine learning to assess one or more of a patient's biomarkers to analyze various conditions, including cancers, such as breast cancer. The present systems and methods can be trained to analyze patient's biomarker data to form prognoses, diagnoses, and treatment suggestions. Further, the present systems and methods can use biomarker feature data and clinical feature data to create novel correlations in order to provide more accurate, patient-specific diagnoses, prognoses, and treatment suggestions.

37 Claims, 5 Drawing Sheets

(51) Int. Cl.
| | |
|---|---|
| *G06T 7/00* | (2017.01) |
| *G06T 7/11* | (2017.01) |
| *G16B 40/00* | (2019.01) |
| *G16H 10/40* | (2018.01) |
| *G16H 50/20* | (2018.01) |
| *G16H 50/30* | (2018.01) |
| *G16H 50/70* | (2018.01) |
| *G16H 15/00* | (2018.01) |

(52) U.S. Cl.
CPC ............. *G16B 40/00* (2019.02); *G16H 10/40* (2018.01); *G16H 50/20* (2018.01); *G16H 50/30* (2018.01); *G16H 50/70* (2018.01); *G06T 2207/10056* (2013.01); *G06T 2207/20081* (2013.01); *G06T 2207/20084* (2013.01); *G06T 2207/30024* (2013.01); *G06T 2207/30096* (2013.01); *G16H 15/00* (2018.01)

(58) Field of Classification Search
CPC ........ G16H 50/30; G16H 50/70; G16H 15/00; G16H 30/40
See application file for complete search history.

(56) References Cited

U.S. PATENT DOCUMENTS

| | | | |
|---|---|---|---|
| 2013/0143747 | A1 | 6/2013 | Gutin |
| 2018/0148790 | A1 | 5/2018 | Ayers et al. |
| 2019/0048425 | A1 | 2/2019 | Shuber |
| 2019/0156159 | A1* | 5/2019 | Kopparapu ....... G06F 18/24147 |
| 2019/0161803 | A1 | 5/2019 | Lenz |
| 2019/0218558 | A1 | 7/2019 | Greco |
| 2020/0115762 | A1 | 4/2020 | Khammanivong et al. |

FOREIGN PATENT DOCUMENTS

| | | | |
|---|---|---|---|
| WO | 2012106718 | A2 | 8/2012 |
| WO | 2017181146 | A1 | 10/2017 |
| WO | 2019/094780 | A2 | 5/2019 |
| WO | WO-2020014477 | A1 * | 1/2020 |
| WO | 2020/080891 | A1 | 4/2020 |
| WO | 2020113237 | A1 | 6/2020 |

OTHER PUBLICATIONS

Best, 2015, RNA-Seq of tumor-educated platelets enables blood-based pan-cancer, multiclass, and molecular pathway cancer diagnostics, Cancer Cell 28(5):666-676.

Campanella, 2019, Clinical-grade computational pathology using weakly supervised deep learning on whole slide mages, Nat Med 25:1301-1309.

Cardoso, 2016, 70-Gene signature as an Aid to treatment cecisions in early-stage breast cancer, NEJM 375(8):717-729.

Cheerla, 2019, Deep learning with multimodal representation for pancancer prognosis prediction, Bioinformatics 35(14):i446-i454.

Chin, 2019, Detection of solid tumor molecular residual disease (MRD) using circulating tumor DNA (ctDNA), Molecular Diag Ther 23(3):311-331.

Garcia-Murillas, 2015, Mutation tracking in circulating tumor DNA predicts relapse in early breast cancer, Sci Trans Med 7(302):302ra133.

Grant, 2019, Reclassification of early stage breast cancer into treatment groups by combining the use of Immunohistochemistry and microarray analysis, WiSWB 2018, 115(3/4), 6 pages.

Graveel, 2015, Critical analysis of the potential for microRNA biomarkers in breast cancer management, Breast Cancer: Targets and Therapy, 7:59-79.

Louie, 2017, Review Article Steroid hormone receptors as prognostic markers in breast cancer, Am J Cancer Res, pp. 1617-1636.

Mittempergher, 2020, Performance characteristics of the BluePrintÒ breast cancer diagnostic test, Trans Oncol 13(4):100756.

Mosly, 2018, Predictive markers of endocrine response in breast cancer, World Journal of Experimental Medicine Introduction, World J Exp Med, 8(1):1-7.

Narasimhan, 2003, Prediction Analysis of Microarrays in Excel, Proceedings of DSC, 11 pages.

Parker, 2009, Supervised Risk Predictor of Breast Cancer Based on Intrinsic Subtypes, Journal of Clinical Oncology, 27(8):1160-1167.

Salvadores, 2019, Passenger mutations acurately xlassify human tumors, PLOS Comp Biol 15(4):e1006953.

Tian, 2010, Biological Functions of the Genes in the Mammaprint Breast Cancer Profile Reflect the Hallmarks of Cancer, Biomarker Insights, 5:129-138.

Wahl, 2020, The interaction of genomics, molecular imaging, and therapy in gastrointestinal tumors, Sem Nucl Med 50(5):471-483.

Xi, 2017, RNA Biomarkers: Frontier of Precision Medicine for Cancer, Non-Coding RNA, 3(1), 17 pages.

Yoon, 2020, Hormone Receptor-Status Prediction in Breast Cancer Using Gene Expression Profiles and Their Macroscopic Landscape, Cancers, 12(5):1165.

Zhao, 2018, Clinical and Genomic Implications of Luminal and Basal Subtypes Across Carcinomas, Clin Cancer Res, 25(8):2450-2457.

Chaudhuri et al, 2017, Early Detection of Molecular Residual Disease in Localized Lung Cancer by Circulating Tumor DNA Profiling, 7(12): 1394-1403.

Sun, 2019, A Multimodal Deep Neural Newtork for Human Breast Cancer Prognosis Prediction by Integrating Multi- Dimensional Data, 16(3), 841-850.

Waaseth, 2011, Sex hormones and gene expression signatures in peripheral blood from postmenopausal women- the NOWAC postgenome study, BMC Medical Genomics.

Cauley, 1999, Elevated serum estradiol and testosterone concentrations are associated with a high risk for breast cancer, Ann Intern Med 130:270-277.

Talia, 2020, The G Protein-Coupled Estrogen Receptor (GPER) expression correlates with pro-metastatic pathways in ER-negative breast cancer: A bioinformatics analysis, Cells 9(3):622.

Perez Garcia, 2018, Targeting FGFR pathway in breast cancer, Breast 37:126-133.

Bosl, 2017, MammaPrint versus EndoPredict: Poor correlation in disease recurrence risk classification of hormone receptor positive breast cancer, Plos One, 12(8):e0183458.

Tewes et al., 2009, Molecular profiling and predictive value of circulating tumor cells in patients with metastatic breast cancer: an option for monitoring response to breast cancer related therapies, Breast Cancer Research and Treatment, 225, 581-590.

Smirnov et al., 2005, Global Gene Expression Profiling of Circulating Tumor Cells, Cancer Res, 65(12), 4993-4997.

International Search Report and Written Opinion issued in International Application No. PCT/IB2021/000521, dated Oct. 2, 2022.

International Search Report and Written Opinion issued in International Application No. PCT/IB2021/000540, dated Dec. 7, 2021.

International Search Report and Written Opinion issued in International Application No. PCT/IB2021/000520, dated Dec. 12, 2021.

International Search Report and Written Opinion issued in International Application No. PCT/IB2021/000512, dated Jan. 5, 2022.

International Search Report and Written Opinion issued in International Application No. PCT/IB2021/000529, dated Dec. 23, 2021.

International Search Report and Written Opinion issued in International Application No. PCT/IB2021/000542, dated Nov. 7, 2022.

International Search Report and Written Opinion issued in International Application No. PCT/IB2023/000255, dated Oct. 24, 2023.

* cited by examiner

METHODS OF ASSESSING DISEASES USING IMAGE CLASSIFIERS

TECHNICAL FIELD

The present disclosure relates to methods and systems for using multiple image classifiers to analyze various conditions, including cancers, such as breast cancer.

BACKGROUND

Breast cancer is the second most common cancer among women in the United States. Recent studies have shown that there are racial/ethnic variations in breast cancer tumor characteristics, subtypes, relative treatment success rates, and recurrence rates. Moreover, the efficacy of various treatments diverges amongst breast cancer subtypes at various stages of progression. This creates a complex picture for pathologists and oncologists in diagnosing, treating, and predicting recurrence in breast cancer patients.

Although breast cancers come in myriad forms and presentations, they are generally classified based upon histological appearance, i.e., using histopathological practices. This generally means a biopsy followed by a microscopic whole-slide image (WSI) analysis. However, this is a time consuming and difficult process, which is prone to human errors and biases. Various molecular analysis assays have also been introduced to diagnose, type, and stage breast cancer. Though, in principle, these assays should be more objective than visual histopathology, they too come with their own limitations.

Recently, the present inventors combined histopathology and molecular analysis using machine learning to classify and diagnose cancer. For example, as disclosed in U.S. Provisional Application No. 63/062,102, which is incorporated herein by reference. However, in certain instances, such an approach can lead to ambiguous results. This is especially true when a patient's histopathology and/or molecular analysis data does not contain, or contains both, features clearly correlated with a positive or negative cancer diagnosis

SUMMARY

The present invention provides systems and methods for assessing diseases in a subject by analyzing a tissue sample image using more than one image classifier, each trained using a different data set. The present Inventors discovered that assessing diseases using a single image classifier to analyze tissue sample images could generate ambiguous results. For example, when assessing breast cancer risk, an ambiguous result could mean that a patient could not be determined to be at either a high or low risk for developing cancer with sufficient confidence. However, the present Inventors found that, surprisingly, by employing more than one image classifier, each trained using a different data set, tissue sample images that provided ambiguous results when analyzed using a single image classifier could provide a definite an meaningful diagnosis, prognosis, and/or risk assessment of a disease in a subject when analyzed by multiple classifiers.

In certain aspects, the invention provides a method for assessing cancer risk. The method includes training a first image classifier to correlate biomarker data from tissue samples to features in images of the tissue samples. An image of a tissue sample from a subject is provided to the first image classifier and the image is analyzed (using the first image classifier) to generate a first cancer risk score. If the first cancer risk score does not deviate from a threshold, the image is analyzed using at least a second image classifier to generate at least a second cancer risk score. The method includes classifying a level of cancer risk for the subject using the first and at least second cancer risk scores. The method preferably includes training the second image classifier to correlate biomarker data from tissue samples to features in images of the tissue samples using at least a second set of training data. In some embodiments, the first set of training data comprises biomarker data and tissue sample images correlated with a cancer risk between a high and low cancer risk; and the second set of training data consists of biomarker data and tissue sample images correlated with at least a high and/or low cancer risk. The first set of training data may further include biomarker data and tissue sample images correlated with a high and/or low cancer risk. The threshold is said to be surpassed when the first cancer risk score indicates a high or a low cancer risk.

The method may further include training one or more additional image classifiers to correlate biomarker data from tissue samples to features in images of the tissue samples using at least a different set of training data for each classifier. If the first cancer risk score does not deviate from a threshold, the image may be analyzed using the additional image classifiers to generate additional cancer risk scores. Classifying may include using the first, second, and additional cancer risk scores.

In preferred embodiments, the cancer risk scores are assigned to a group, wherein each group corresponds to a different range of cancer risk scores. The second set of training data may consist of biomarker data (e.g., microarray data showing expression of a panel of genes) and tissue sample images (e.g., whole-slide images from stained tumor sections) correlated with a cancer risk score within the cancer risk score range of one or more selected groups. Preferably the selected groups consist of a group with a highest range of cancer risk scores and a group with a lowest range of cancer risk scores.

The method may further include training one or more additional image classifiers to correlate biomarker data from tissue samples to features in images of the tissue samples using at least a different set of training data for each classifier; and if the first cancer risk score does not deviate from a threshold, the image is analyzed using the additional image classifiers to provide additional cancer risk scores.

The risk scores may be grouped into, e.g., at least five groups, which may include a first group with a range cancer risk scores correlated with an ultra-high risk of cancer a second group with a range of cancer risk scores correlated with a high risk of cancer a third group with a range of cancer risk scores correlated with an ambiguous risk of cancer a fourth group with a range of cancer risk scores correlated with a low risk of cancer; and a fifth group with a range of cancer risk scores correlated with an ultra-low risk of cancer. If the first cancer risk score falls within the range of the third group, the first cancer score does not deviate from the threshold.

In some embodiments, training the second and additional classifiers further includes: dividing each of the groups into at least two subdivisions, each subdivision corresponding to a different range of cancer risk scores; and training each of the second and additional classifiers using biomarker data and tissue sample images correlated with a cancer risk score within one or more of the subdivisions. Methods of the disclosure may further include segmenting the tissue image from the subject into segments providing the segments to the image classifiers for analysis to generate cancer risk scores; and classifying a level of cancer risk for the subject using the generated cancer risk scores for each segment.

The biomarker data may include genomic data and/or RNA expression data. RNA expression data may include RNA expression levels determined using sequencing or microarray analysis. In some embodiments RNA expression levels are determined by interrogating a sample with probes specific for a panel of genes and measuring expression levels for positive probe responses.

Aspects of the invention provide a method for assessing cancer risk. The method includes providing an image of a tissue sample from a patient to an image classifier trained on a plurality of tissue images, each associated with a cancer risk score. The image classifier operates on the image to output a risk score for the patient. When the risk score is within a range of threshold values between high-risk and low-risk scores, the image is provided to a second classifier that has been trained using a selected subset of the plurality of tissue images to obtain a second risk score for the patient. Alternatively, or in addition, the second classifier may be trained using different tissue images, genomic characteristics, phenotypic characteristics or biomarker characteristics to obtain the second risk score.

The present invention also provides a method for assessing risk that includes providing an image of a tissue sample from a patient to an image classifier trained on a plurality of tissue images, each image associated with a cancer risk score. Then, operating the image classifier on the image to output a risk score for the patient. When the risk score is within a range of threshold values between high-risk and low-risk scores, providing the image to a second classifier that has been trained using a selected subset of the plurality of tissue images to obtain a second risk score for the patient.

The image classifier may be trained by CLustering-constrained Attention Multiple instance (CLAM) learning. In some embodiments, the image is a digital whole-slide image (WSI) of a stained section of tissue on a slide. Preferably the section includes tumor tissue and healthy stroma from the patient. The cancer risk score associated with each of the plurality of tissue images may be obtained by a genomic analysis for expression of a panel of genes. The genomic analysis may be selected from arrays, next generation sequencing, PCR, RNAseq, and hybrid capture. In certain embodiments, the second classifier has been trained by including only those images of the plurality of tissue images associated with a very high or very low risk score.

The image classifier may operate using a neural network or random forest.

In certain embodiments, the image classifier divides the image into segments, scores each segment, identifies highest- and lowest-scoring segments, and calibrates scores for remaining segments based on the highest- and lowest-scoring segments. The cancer risk scores associated with the plurality of tissue images may be divided into groups that include at least a highest risk group, a middle group for the range of threshold values between high-risk and low-risk scores, and a lowest risk group. Then, preferably, the selected subset of the plurality of tissue images does not include any images associated with scores in the middle group.

In some embodiments, the cancer risk scores associated with the plurality of tissue images are divided into a number of groups such that a cutoff value between a positive and a negative cancer risk score lies within one group and not an a boundary between two groups. The selected subset of the plurality of tissue images can then be selected to not include any images associated with scores in the one group.

Methods may include pre-processing the image before operating the image classifier to select and include regions containing only certain tissue types. The image classifier may compute an attention map for the included regions. The image classifier may trained on a plurality of tissue images that includes at least ten thousand images.

DETAILED DESCRIPTION

The present disclosure relates to methods and systems for assessing a disease risk by analyzing an image of a tissue sample from a subject using multiple image classifiers, each trained using a different data set. Surprisingly, by using multiple image classifiers, each trained with a different data set, the claimed methods and systems can provide more accurate and precise disease risk assessments. The methods and systems can make such assessments, even using images that provided an ambiguous disease risk when using a single image classifier. Thus, the methods and systems can even use existing tissue sample images to provide an accurate and precise disease risk assessment. This obviates the need to obtain a second sample from a patient, which may prove difficult (e.g., due to patient follow up, cost, or discomfort) or impossible (e.g., from a tumor that has already been removed and analyzed).

The image classifiers of the invention are trained using data sets of tissue sample images with a paired disease risk scores. A disease risk score may indicate the probability of a certain prognosis and/or diagnosis. The disease risk score may be, for example, an annotation about a feature in the tissue sample image and its association with a disease risk score. The disease risk score can also be based on one or more biomarkers associated with the tissue sample.

Biomarkers may include, for example, RNA expression data. RNA expression panels, such as MammaPrint and BluePrint are used to provide a disease risk assessment, in particular, for breast cancer. Such panels can be used to type or stage a breast cancer. They can also be used, for example, to predict whether a cancer will be recurrent or metastasize, or whether a patient will be diagnosed with cancer. The RNA expression data across the genes in each panel is correlated with the known clinical outcomes of subjects who previously has their RNA expression levels measured. Thus, a patient's individual RNA expression levels, across multiple genes, provides a probability of a particular diagnosis or prognosis, i.e., a disease risk score. Using an image classifier, these scores can be correlated with a tissue sample images obtained from the subjects who had their RNA expression measured.

However, using a single image classifier trained on such images can provide ambiguous disease risk assessments for certain tissue sample images. In these ambiguous risk assessments, the single image classifier may, for example, not be able to identify a feature associated with a high or low risk disease score with a sufficient level of confidence. Similarly, an ambiguous assessment can arise when the classifier detects multiple features in an image, but they include features with high and low disease risk scores. The systems and methods of the disclosure can provide precise and accurate disease assessments of these images that previously provided ambiguous assessments using a single classifier.

Alternatively or in addition, the second classifier can be trained on a data set comprising tissue images, genomic characteristics, phenotypic characteristics or biomarker characteristics to obtain a second risk score for the patient.

The systems and methods of the disclosure achieve this accuracy and precision through multiple image classifiers.

Figure 1:
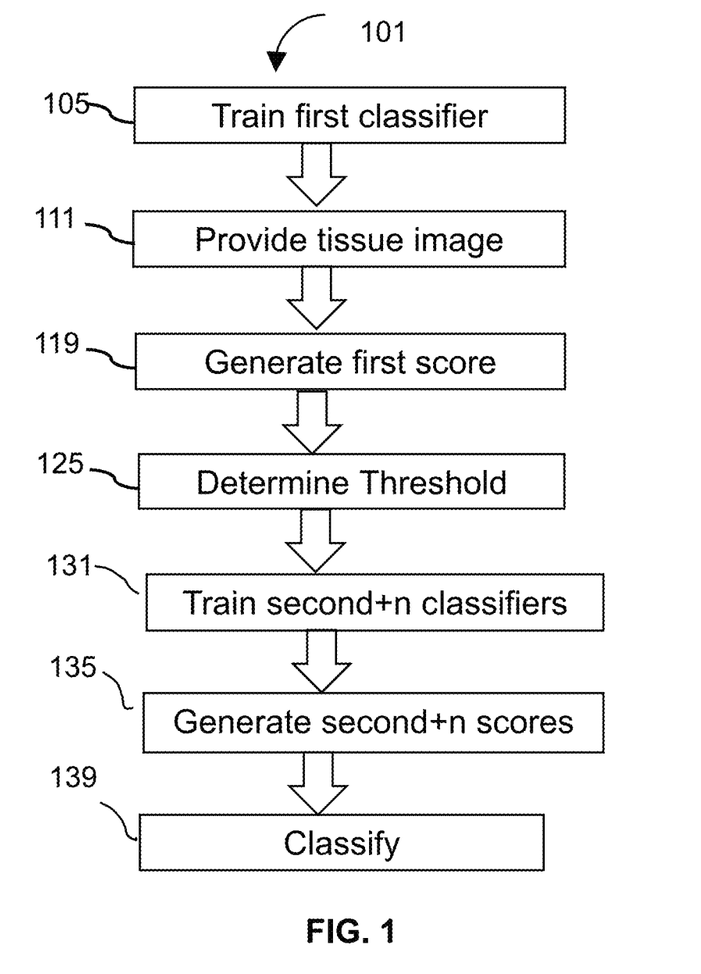
FIG. 1 shows a workflow according to the disclosure.

FIG. 1 diagrams a general workflow used in the methods and systems of the present disclosure. The workflow 101 includes training 105 a first image classifier with tissue sample images associated with a particular disease risk score. This training may include correlating biomarker data from tissue samples associated with a risk score to features in images of the tissue samples. Biomarkers may include, for example, RNA expression data. The biomarkers are paired with a known clinical risk and/or outcome score. Thus, when the image classifier correlates a biomarker with a feature in a tissue, it is creating a probative relationship between an image feature, the biomarker, and ultimately, a probability of particular clinical outcome.

An image of a tissue sample from a subject is provided 111 to the first classifier. A tissue image may include, for example, a whole-slide image (WSI) of a stained tumor section. The image classifier identifies features in the tissue image that are associated with a particular disease risk score, including those associated with certain biomarkers. These correlations are used to generate 119 a first risk score. This score represents the likelihood of a particular clinical outcome, such as developing cancer, based on the analysis of the first classifier.

The workflow then requires determining 125 whether the first risk score deviates from a threshold. This threshold represents the confidence level a particular risk score provides for the probability of a certain clinical outcome. Risk scores that deviate from this threshold provide a sufficiently high level of confidence that a particular clinical outcome will occur. In contrast, risk scores that do not deviate from the threshold do not, on their own, provide a clear risk assessment. Thus, they require analysis by one or more additional image classifiers.

If the first risk score does not deviate from the threshold, the workflow requires training 131 at least a second image classifier, though additional image classifiers may also be trained. The second and additional classifiers are trained 131 using data sets that are different from one another and the first image classifier. The training sets for the second and additional image classifiers differ from the first in that they only include tissue sample images paired with risk scores of a certain minimal or maximal value. This training may include correlating biomarker data from tissue samples associated with a risk score to features in images of the tissue samples. This may include biomarker data from samples correlated with a known risk for a particular clinical outcome. For example, when assessing breast cancer, the second image classifier may be trained using images/biomarker data correlated with a known high and/or low risk of developing breast cancer. In contrast, the first image classifier is trained using data that is agnostic to any particular risk level.

The trained second and additional image classifiers are used to generate 135 an additional risk score, one for each image classifier. The additional risk scores are used in conjunction with the first to classify 139 a level of risk for a particular clinical outcome in the subject.

The present Inventors have found that, surprisingly, tissue images that provide a first risk score that do not deviate from the threshold using only the first image classifier could provide a definite an meaningful diagnosis, prognosis, and/or risk assessment of a disease in a subject when analyzed by multiple image classifiers trained on distinct data sets.

In certain methods and systems of the invention, risk scores are grouped. Each group consists of a range of risk scores within a certain range. For examples, the risk scores may be grouped into least five groups. The first group with a range cancer risk scores correlated with an ultra-high risk of cancer; the second group with a range of cancer risk scores correlated with a high risk of cancer; the third group with a range of cancer risk scores correlated with an ambiguous risk of cancer; the fourth group with a range of cancer risk scores correlated with a low risk of cancer; and a fifth group with a range of cancer risk scores correlated with an ultra-low risk of cancer. If the first cancer risk score falls within the range of the third group, the first cancer score does not deviate from the threshold.

The grouped scores can be used to create the risk-score-based training sets for the second and additional image classifiers. The Inventors have discovered that employing image classifiers trained using different grouped scores, that images that otherwise provided ambiguous risk assessments could be used to provide meaningful predictions.

For example, the Inventors found that training the second and/or additional image classifiers using data from the groups with extreme risk scores, ambiguous results could be remedied. Thus, in certain methods and systems, the second and/or additional image classifiers are trained with training data sets that contain images associated with risk scores in the first and last groups, e.g., the first group and fifth group. Similarly, groups with less extreme risk score ranges, e.g., the second and fourth group, can be used.

Alternatively, the second and additional image classifiers can be trained using only data from a single group. Thus, for example, the second classifier may be trained using the first group, a third classifier using the second group, etc. In such instances, the tissue sample image is analyzed with each classifier, which results in a risk score generated by each classifier. These risk scores, in conjunction with that generated by the first classifier, can be combined to assess the risk for a disease in a subject.

Similarly, each group can be divided into subdivisions, with each division consisting of data with risk scores falling within a certain rage inside the group's range. A classifier can be trained using one or more of these subdivisions.

The systems and methods of the disclosure can be used to provide a predictive output for a diagnosis, prognosis, and/or risk of a disease in a subject. Such predictive outputs may include a metric for each type of biomarker feature analyzed. These metrics may be combined to form a larger prediction. These metrics may be weighted. Predictive outputs may include signature biomarker features for certain types of conditions, for example, an image feature signature or RNA expression signature for a subtype of breast cancer. Predictive outputs may be used to assess disease severity, such as staging breast cancer or predicting the risk of metastasis, recurrence, or residual risk. Predictive outputs may be longitudinal. Longitudinal outputs may be outputs for the same patient or patient population over time, and updated based upon additional biomarker or image feature data and/or clinical data. Predictive outputs may be based upon threshold values for one or more biomarker or image feature data and/or clinical data. Threshold values may be created using machine learning (ML) models or by humans. ML models may be used to provide predictive outputs for various treatment options for particular patients or patient populations. A single tissue sample may be used to provide both image feature data and biomarker feature data to provide predictive outputs for a patient's risk (e.g., likely risk of metastasis for a tumor), relative treatment efficacies, and benefit of further monitoring (e.g., how often the patient should have a tumor analyzed). A single tissue, e.g., a particular tumor, may be monitored at several time points and analyzed using the methods and systems of the invention to provide continual predictive outputs, including a risk score and treatment score.

RNA expression levels are an important biomarker feature analyzed to diagnose and predict clinical outcomes of diseases and conditions, including breast cancer. The methods and systems of the disclosure use RNA expression levels as a biomarker paired with tissue sample images for training the image classifiers. RNA expression profiles from single cells, cellular components, and extracellular components, such as exosomes, have been shown to provide patient-specific clinical prediction. RNA expression profiles can be obtained from extracellular vesicles, which have more stable RNA expression profiles relative cells themselves. This is especially important in the heterogeneous and ever-changing environment of a tumor.

RNA expression levels have been shown to correlate specific disease types and probable clinical outcomes. For example, the BluePrint test (Agendia®) is an 80-gene signature assay that measures the combined RNA expression of 80 genes. This test has consistently been able to classify the majority of tested breast cancer patients into definitive breast cancer clinical subtypes, i.e., Luminal-type, Basal-type, and HER2-type. (Mittempergher et al., *Translational Oncology*, 13 (2020) 100756). For each clinical subtype, a signature RNA expression was determined. A patient's RNA profile is compared to these signature RNA expression levels to determine the patient's clinical subtype. Id. The MammaPrint test (Agendia®) is a 70-gene signature assay that measures the combined RNA expression of 70-genes to assign breast cancer tumors as being of a high or low risk for metastasis. Id. These tests guide a physician's treatment decisions, including whether to pursue early chemotherapy, and avoiding aggressive treatments when they would provide no benefit.

However, the systems and methods of the disclosure can also be used to improve the accuracy and precision of a panel such as BluePrint or MammaPrint in providing clinical predictions.

Figure 5:
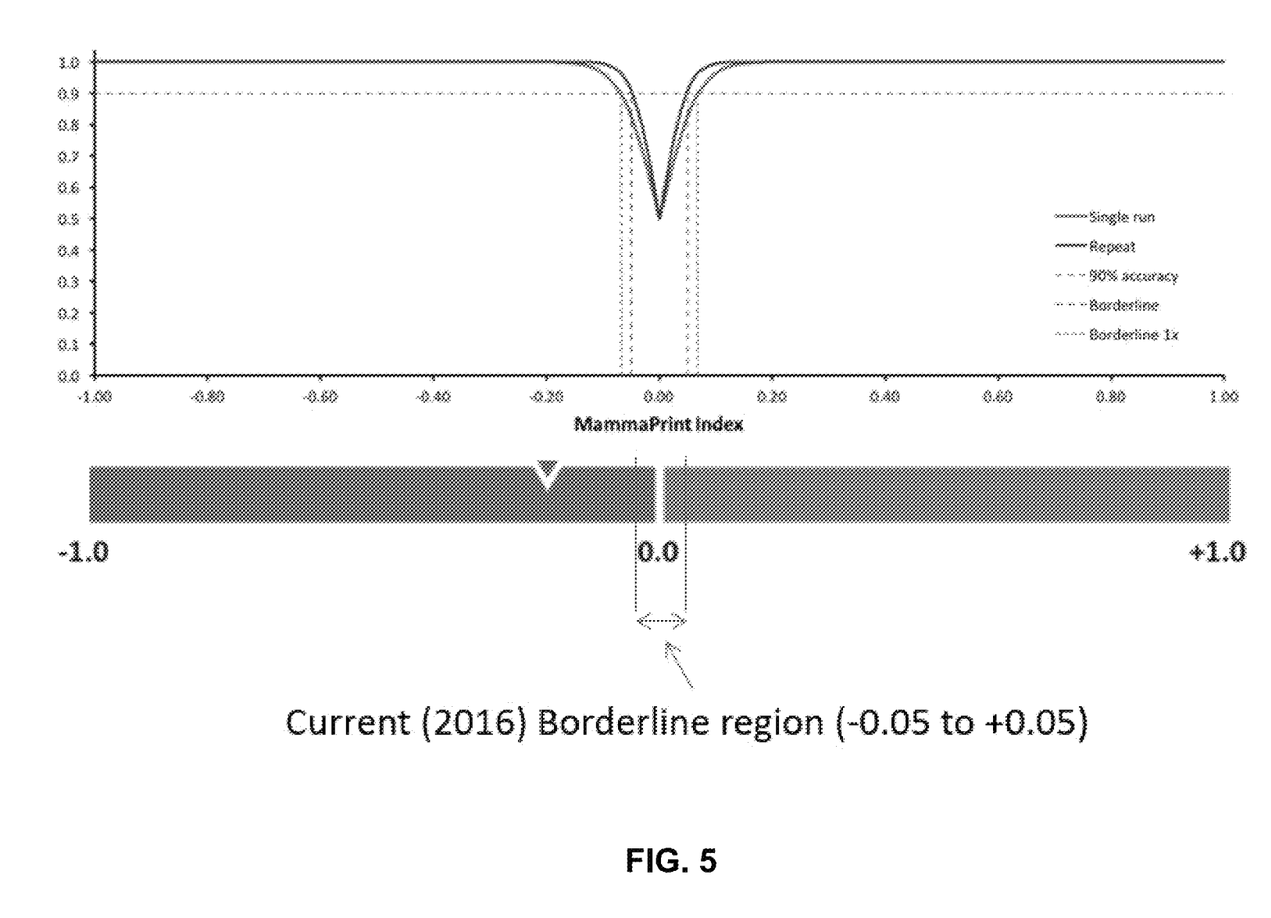
FIG. 5 shows binned risk scores.

FIG. 5 shows the analytical classification accuracy for the MammaPrint panel. The panel provides a continuous risk score for developing breast that ranges from −1 for low risk of cancer to +1 for high risk. The left axis shows the level of confidence in the cancer prediction risk. As shown in FIG. 5, when the panel results in a risk score ranging from about −0.05 to +0.05, confidence levels plummet. The systems and methods of the disclosure can use image feature data and multiple image classifiers to provide a meaningful clinical prediction for those individuals who have a risk score provided by the MammaPrint panel that results in a low confidence level.

Further, as RNA expression profiling becomes faster and more ubiquitous, the systems and methods of the disclosure can be leveraged to expand existing panels or create new panels. For example, using clinical data inputs and expanded RNA expression profiles, the systems and methods can create novel correlations between newly significant genes and clinical data.

Genetics and epigenetics are known to play a key role in a patient's risk for developing a particular disease or condition. For example, certain inherited mutations in the BRCA1 and BRCA2 tumor suppressor genes increase the risk of developing certain types of cancers, including breast cancer. Thus, genetics and epigenetics can be used as a biomarker feature in the methods and systems of the disclosure. Training an image classifier with patients' clinical data and DNA sequence data (biomarker feature data), or portions thereof, an image classifier system can create novel correlations. For example, a classifier can correlate one or more alleles, mutations, copy number mutations, etc. with certain image feature found in patients' tissue sample images. This can be leveraged, for example, to provide predictive outcomes in whether patients will develop a certain condition, how they will respond to various treatments, and predicted clinical outcomes. Genetic and epigenetic data can also be derived from different cancer cells, or from various regions of tumors to ascertain driver and passenger mutations. Further, circulating tumor DNA (ctDNA) can form an important source of biomarker feature data in the methods and systems of the disclosure.

Further, combinations of patients' RNA expression profiles, genetic and/or epigenetic data, and clinical data can be input with tissue sample images into a classifier of the present disclosure to develop novel correlations leading to predictive outcomes. This can improve the accuracy and functional information of existing tests. Further, like RNA expression panels, specific genetic and epigenetic features with specific qualities may be targeted to create more robust and accurate tests.

Another key biomarker feature to accurately form accurate, diagnoses, prognoses, and treatment decisions, especially in breast cancer, is levels of hormones and hormone receptors. For example, the MammaPrint and BluePrint RNA expression tests, although testing expression levels of many different genes, ultimately classify some types of breast cancer in categories related to hormone receptors, e.g., human epidermal growth factor receptor 2 (HER2) status. The hormonal milieu (e.g., levels of various hormones and hormone receptors) can be used to provide disease risk scores to pair with the tissue image date to create correlative signatures for predicted diagnoses and prognoses, including risk scores and staging, in breast cancer.

The hormonal milieu can be directly measured input, e.g., by detecting hormone receptor expression on cells using fluorescence in situ hybridization (FISH). RNA expression of genes related to the hormonal milieu can also be used as used to calculate a risk score.

Figure 2:
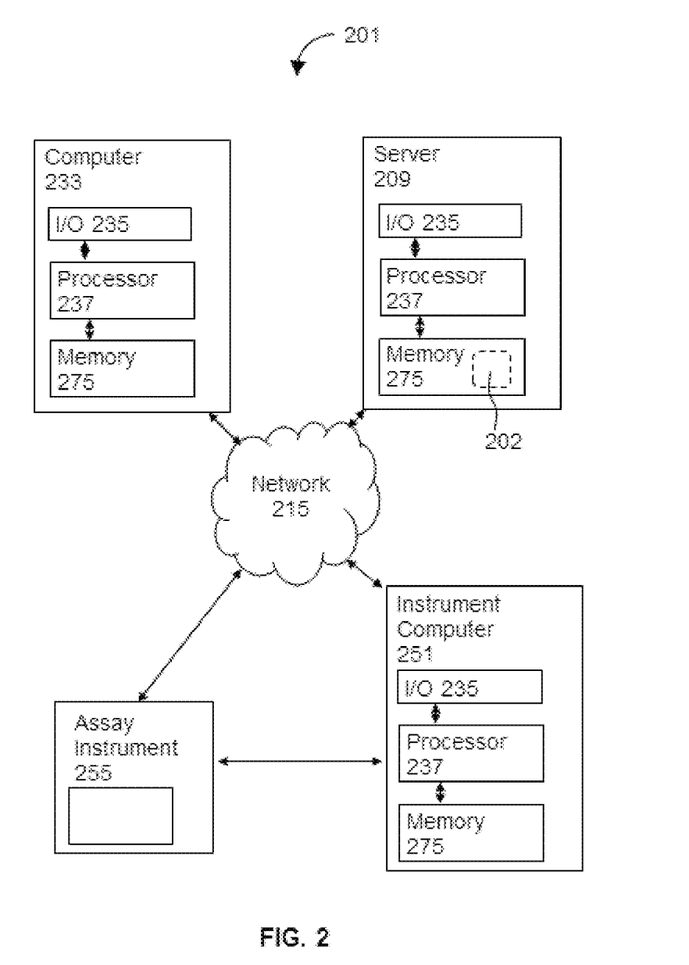
FIG. 2 shows a computer system with an image classifier subsystem.

FIG. 2 shows a computer system 201 that may include an image classifier subsystem 202 with the first and second image classifier and any additional image classifiers that have been trained on training data sets. In preferred embodiments, the subsystem performs the training 105, 131, the generating 119, 135. The system 201 includes at least one processor 237 coupled to a memory subsystem 275 including instructions executable by the processor 237 to cause the system 201 to train and analyze using the subsystem and to provide a disease risk assessment using the disease risk scores.

The system 201 includes at least one computer 233. Optionally, the system 201 may further include one or more of a server computer 209 one or more assay instruments 255 (e.g., a microarray, nucleotide sequencer, an imager, etc.), which may be coupled to one or more instrument computers 251. Each computer in the system 201 includes a processor 237 coupled to a tangible, non-transitory memory 275 device and at least one input/output device 235. Thus the system 201 includes at least one processor 237 coupled to a memory subsystem 275. The components (e.g., computer, server, instrument computers, and assay instruments) may be in communication over a network 215 that may be wired or wireless and wherein the components may be remotely located or located in close proximity to each other. Using those mechanical components, the system 201 is operable to receive or obtain training data such (e.g., images and molecular assay data) and outcome data as well as test sample data generated by one or more assay instruments or otherwise obtained. The system may use the memory to store the received data as well as the machine learning system data which may be trained and otherwise operated by the processor.

Processor refers to any device or system of devices that performs processing operations. A processor will generally include a chip, such as a single core or multi-core chip (e.g., 12 cores), to provide a central processing unit (CPU). In certain embodiments, a processor may be a graphics processing unit (GPU) such as an NVidia Tesla K80 graphics card from NVIDIA Corporation (Santa Clara, CA). A processor may be provided by a chip from Intel or AMD. A processor may be any suitable processor such as the microprocessor sold under the trademark XEON E5-2620 v3 by Intel (Santa Clara, CA) or the microprocessor sold under the trademark OPTERON 6200 by AMD (Sunnyvale, CA). Computer systems of the invention may include multiple processors including CPUs and or GPUs that may perform different steps of methods of the invention.

The memory subsystem 275 may contain one or any combination of memory devices. A memory device is a mechanical device that stores data or instructions in a machine-readable format. Memory may include one or more sets of instructions (e.g., software) which, when executed by one or more of the processors of the disclosed computers can accomplish some or all of the methods or functions described herein. Preferably, each computer includes a non-transitory memory device such as a solid state drive, flash drive, disk drive, hard drive, subscriber identity module (SIM) card, secure digital card (SD card), micro SD card, or solid-state drive (SSD), optical and magnetic media, others, or a combination thereof.

Using the described components, the system 201 is operable to produce a report and provide the report to a user via an input/output device. An input/output device is a mechanism or system for transferring data into or out of a computer. Exemplary input/output devices include a video display unit (e.g., a liquid crystal display (LCD) or a cathode ray tube (CRT)), a printer, an alphanumeric input device (e.g., a keyboard), a cursor control device (e.g., a mouse), a disk drive unit, a speaker, a touchscreen, an accelerometer, a microphone, a cellular radio frequency antenna, and a network interface device, which can be, for example, a network interface card (NIC), Wi-Fi card, or cellular modem. The subsystem 202 has preferably trained on training data that includes training images and known risk scores.

Systems of the invention may be configured to assay data, and known outcomes, to identify features within assay data in an unsupervised manner and to create a map of outcome probabilities over features in the assay data. The system can further receive assay data from a test subject, identify within the assay data predictive features learned from the training steps and locate the predictive features on the map of outcome probabilities to provide a prognosis or diagnosis.

Any of several suitable types of machine learning may be used for one or more steps of the disclosed methods and systems. Suitable machine learning types may include neural networks, decision tree learning such as random forests, support vector machines (SVMs), association rule learning, inductive logic programming, regression analysis, clustering, Bayesian networks, reinforcement learning, metric learning, and genetic algorithms. One or more of the machine learning approaches (aka type or model) may be used to complete any or all of the method steps described herein.

For example, one model, such as a neural network, may be used to complete the training steps of autonomously identifying features and associating those features with certain outcomes. Once those features are learned, they may be applied to test samples by the same or different models or classifiers (e.g., a random forest, SVM, regression) for the correlating steps. In certain embodiments, features may be identified and associated with outcomes using one or more machine learning systems and the associations may then be refined using a different machine learning system. Accordingly some of the training steps may be unsupervised using unlabeled data while subsequent training steps (e.g., association refinement) may use supervised training techniques such as regression analysis using the features autonomously identified by the first machine learning system.

In decision tree learning, a model is built that predicts that value of a target variable based on several input variables. Decision trees can generally be divided into two types. In classification trees, target variables take a finite set of values, or classes, whereas in regression trees, the target variable can take continuous values, such as real numbers. Examples of decision tree learning include classification trees, regression trees, boosted trees, bootstrap aggregated trees, random forests, and rotation forests. In decision trees, decisions are made sequentially at a series of nodes, which correspond to input variables. Random forests include multiple decision trees to improve the accuracy of predictions. See Breiman, 2001, Random Forests, Machine Learning 45:5-32, incorporated herein by reference. In random forests, bootstrap aggregating or bagging is used to average predictions by multiple trees that are given different sets of training data. In addition, a random subset of features is selected at each split in the learning process, which reduces spurious correlations that can results from the presence of individual features that are strong predictors for the response variable. Random forests can also be used to determine dissimilarity measurements between unlabeled data by constructing a random forest predictor that distinguishes the observed data from synthetic data. Id.; Shi, T., Horvath, S. (2006), Unsupervised Learning with Random Forest Predictors, Journal of Computational and Graphical Statistics, 15(1):118-138, incorporated herein by reference. Random forests can accordingly by used for unsupervised machine learning methods of the invention.

SVMs are useful for both classification and regression. When used for classification of new data into one of two categories, such as having a disease or not having the disease, a SVM creates a hyperplane in multidimensional space that separates data points into one category or the other. Although the original problem may be expressed in terms that require only finite dimensional space, linear separation of data between categories may not be possible in finite dimensional space. Consequently, multidimensional space is selected to allow construction of hyperplanes that afford clean separation of data points. See Press, W. H. et al., Section 16.5. Support Vector Machines. Numerical Recipes: The Art of Scientific Computing (3rd ed.). New York: Cambridge University (2007), incorporated herein by reference. SVMs can also be used in support vector clustering to perform unsupervised machine learning suitable for some of the methods discussed herein. See Ben-Hur, A., et al., (2001), Support Vector Clustering, Journal of Machine Learning Research, 2:125-137.

Regression analysis is a statistical process for estimating the relationships among variables such as features and outcomes. It includes techniques for modeling and analyzing relationships between a multiple variables. Specifically, regression analysis focuses on changes in a dependent variable in response to changes in single independent variables. Regression analysis can be used to estimate the conditional expectation of the dependent variable given the independent variables. The variation of the dependent variable may be characterized around a regression function and described by a probability distribution. Parameters of the regression model may be estimated using, for example, least squares methods, Bayesian methods, percentage regression, least absolute deviations, nonparametric regression, or distance metric learning.

Association rule learning is a method for discovering interesting relations between variables in large databases. See Agrawal, 1993, Mining association rules between sets of items in large databases, Proc 1993 ACM SIGMOD Int Conf Man Data p. 207, incorporated by reference. Algorithms for performing association rule learning include Apriori, Eclat, FP-growth, and AprioriDP. FIN, PrePost, and PPV, which are described in detail in Agrawal, 1994, Fast algorithms for mining association rules in large databases, in Bocca et al., Eds., Proceedings of the 20th International Conference on Very Large Data Bases (VLDB), Santiago, Chile, September 1994, pages 487-499; Zaki, 2000, Scalable algorithms for association mining, IEEE Trans Knowl Data Eng 12(3):372-390; Han, 2000, Mining Frequent Patterns Without Candidate Generation, Proc 2000 ACM SIGMOD Int Conf Management of Data; Bhalodiya, 2013, An Efficient way to find frequent pattern with dynamic programming approach, NIRMA Univ Intl Conf Eng, 28-30 Nov. 2013; Deng, 2014, Fast mining frequent itemsets using Nodesets, Exp Sys Appl 41(10):4505-4512; Deng, 2012, A New Algorithm for Fast Mining Frequent Itemsets Using N-Lists, Science China Inf Sci 55(9): 2008-2030; and Deng, 2010, A New Fast Vertical Method for Mining Frequent Patterns, Int J Comp Intel Sys 3(6):333-344, the contents of each of which are incorporated by reference. Inductive logic programming relies on logic programming to develop a hypothesis based on positive examples, negative examples, and background knowledge. See Luc De Raedt. A Perspective on Inductive Logic Programming. The Workshop on Current and Future Trends in Logic Programming, Shakertown, to appear in Springer LNCS, 1999; Muggleton, 1993, Inductive logic programming: theory and methods, J Logic Prog 19-20:629-679, incorporated herein by reference.

Bayesian networks are probabilistic graphical models that represent a set of random variables and their conditional dependencies via directed acyclic graphs (DAGs). The DAGs have nodes that represent random variables that may be observable quantities, latent variables, unknown parameters or hypotheses. Edges represent conditional dependencies; nodes that are not connected represent variables that are conditionally independent of each other. Each node is associated with a probability function that takes, as input, a particular set of values for the node's parent variables, and gives (as output) the probability (or probability distribution, if applicable) of the variable represented by the node. See Charniak, 1991, Bayesian Networks without Tears, AI Magazine, p. 50, incorporated by reference.

Preferably one or more image classifiers are trained by image classifier is trained by CLustering-constrained Attention Multiple instance (CLAM) learning or a modified CLAM learning. CLAM employs a hybrid metaheuristic between Tabu search VNS, thereby solving k-medoid clustering. CLAM is a deep-learning model that is weakly-supervised. It can use attention-based learning to automatically identify sub-regions of higher predictive value to accurately classify an entire whole tissue sample image. It concurrently uses instance-level clustering over representative regions identified that constrain and refine a feature space.

Figure 3:
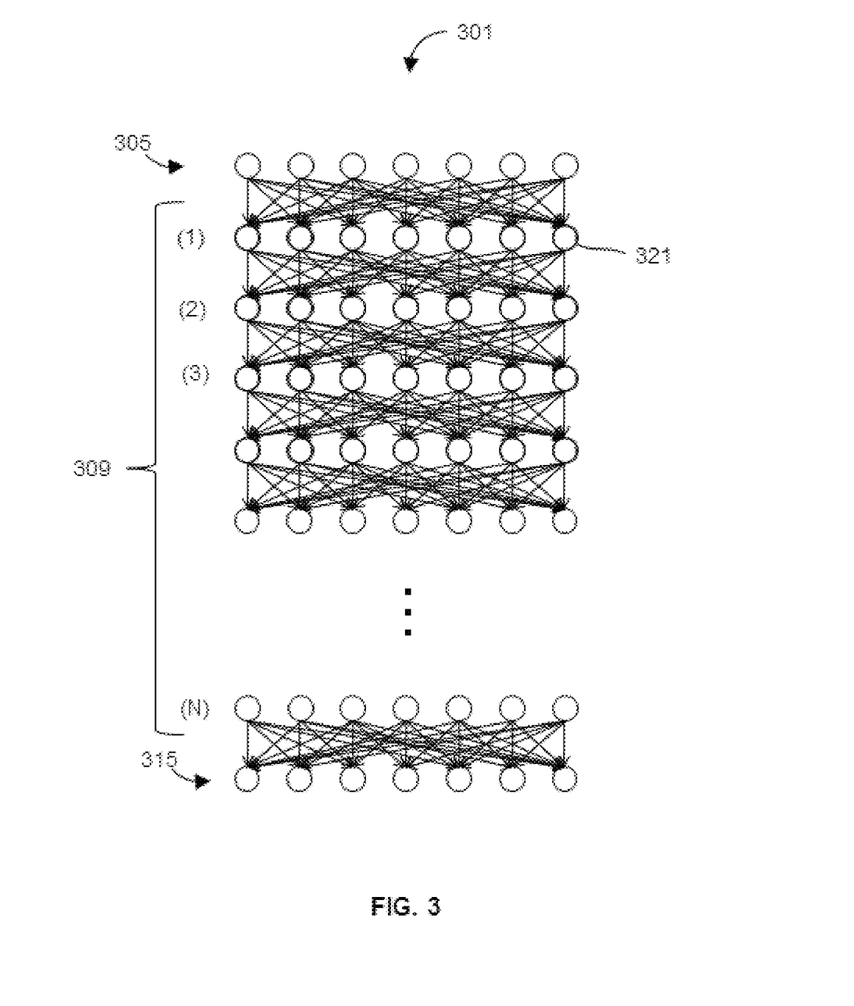
FIG. 3 illustrates a deep-learning neural network.

A neural network, which is modeled on the human brain, allows for processing of information and machine learning. The neural network 301 includes nodes 321 that mimic the function of individual neurons, and the nodes are organized into layers. The neural network includes an input layer, an output layer, and one or more hidden layers that define connections from the input layer to the output layer. The neural network may, for example, have multiple nodes in the output layer and may have any number of hidden layers. The total number of layers in a neural network depends on the number of hidden layers. For example, the neural network may include at least 5 layers, at least 10 layers, at least 15 layers, at least 20 layers, at least 25 layers, at least 30 layers, at least 40 layers, at least 50 layers, or at least 100 layers. The nodes of the neural network serve as points of connectivity between adjacent layers. Nodes in adjacent layers form connections with each other, but nodes within the same layer do not form connections with each other. The neural network 301 has an input layer 305, n hidden layers 309, and an output layer 315. Each layer may comprise a number of nodes 321.

The system may include any neural network that facilitates machine learning. The system may include a known neural network architecture, such as GoogLeNet (Szegedy, et al. Going deeper with convolutions, in CVPR 2015, 2015); AlexNet (Krizhevsky, et al. Imagenet classification with deep convolutional neural networks, in Pereira, et al. Eds., Advances in Neural Information Processing Systems 25, pages 1097-3105, Curran Associates, Inc., 2012); VGG16 (Simonyan & Zisserman, Very deep convolutional networks for large-scale image recognition, CoRR, abs/3409.1556, 2014); or FaceNet (Wang et al., Face Search at Scale: 90 Million Gallery, 2015), each of the aforementioned references are incorporated by reference.

Training data includes data relevant to the assay data which the neural network will analyze, which may be annotated with known outcomes. Nodes in the input layer receive assay data from one or more individuals. For example, the nodes may receive tissue images or portions thereof, such as patches or geometric shapes from within tissue images. The known outcomes associated with the training images are provided to the neural network.

Deep learning (also known as deep structured learning, hierarchical learning or deep machine learning) is a class of machine learning operations that use a cascade of many layers of nonlinear processing units for feature extraction and transformation. Each successive layer uses the output from the previous layer as input. The algorithms may be supervised or unsupervised and applications include pattern analysis (unsupervised) and classification (supervised). Certain embodiments are based on unsupervised learning of multiple levels of features or representations of the data. Higher level features are derived from lower level features to form a hierarchical representation. Those features are preferably represented within nodes as feature vectors.

Figure 4:
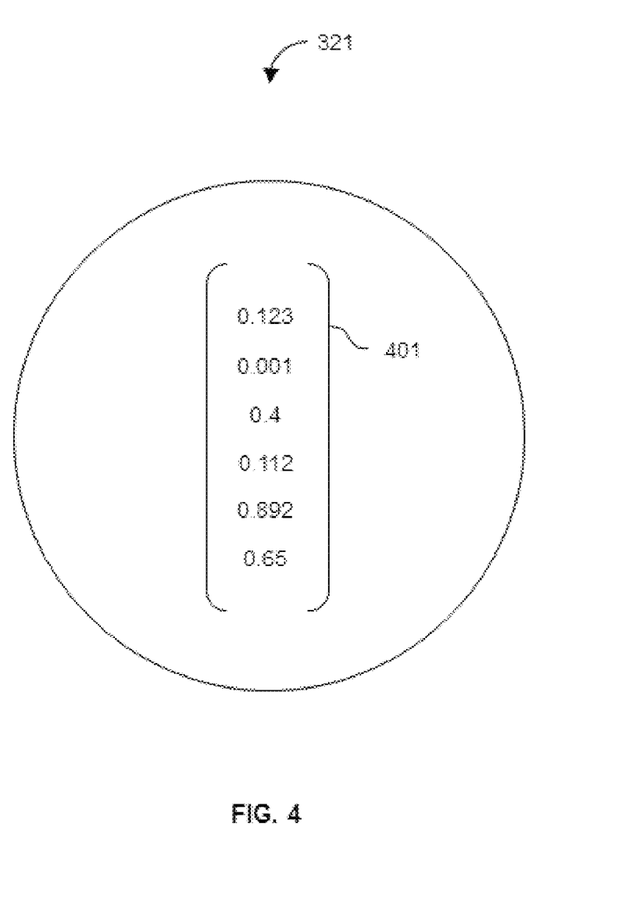
FIG. 4 shows a feature vector in a neural network.

FIG. 4 shows a feature vector 401 representing a feature within a node 321 in a layer of the neural network. Nodes of the neural network may comprise feature vectors 401. Feature vectors may be n-dimensional vectors of numerical features that represent an object. Feature vectors may correspond to pixels, such as in a WSI, and may further represent detected characteristics in the pixels. Feature vectors may be combined with weights using a dot product in order to construct a linear predictor function that is used to determine a score for making a prediction.

Deep learning by the neural network includes learning multiple levels of representations that correspond to different levels of abstraction; the levels form a hierarchy of concepts. In most preferred embodiments, the neural network includes at least 5 and preferably more than 10 hidden layers. The many layers between the input and the output allow the system to operate via multiple processing layers.

Deep learning is part of a broader family of machine learning methods based on learning representations of data. An observation (e.g., an image) can be represented in many ways such as a vector of intensity values per pixel, or in a more abstract way as a set of edges, regions of particular shape, etc. Those features are represented at nodes in the network. Preferably, each feature is structured as a feature vector, a multi-dimensional vector of numerical features that represent some object. The feature provides a numerical representation of objects, since such representations facilitate processing and statistical analysis. Feature vectors are similar to the vectors of explanatory variables used in statistical procedures such as linear regression. Feature vectors are often combined with weights using a dot product in order to construct a linear predictor function that is used to determine a score for making a prediction.

The vector space associated with those vectors may be referred to as the feature space. In order to reduce the dimensionality of the feature space, dimensionality reduction may be employed. Higher-level features can be obtained from already available features and added to the feature vector, in a process referred to as feature construction. Feature construction is the application of a set of constructive operators to a set of existing features resulting in construction of new features.

Within the network 301, nodes 321 are connected in layers, and signals travel from the input layer to the output layer. In certain embodiments, each node 321 in the input layer 305 corresponds to a respective one of the patches from the training data. The nodes 321 of the hidden layer 309 are calculated as a function of a bias term and a weighted sum of the nodes of the input layer, where a respective weight is assigned to each connection between a node of the input layer and a node in the hidden layer. The bias term and the weights between the input layer and the hidden layer are learned autonomously in the training of the neural network. The network 301 may include thousands or millions of nodes 321 and connections. Typically, the signals and state of artificial neurons are real numbers, typically between 0 and 1. Optionally, there may be a threshold function or limiting function on each connection and on the unit itself, such that the signal must surpass the limit before propagating. Back propagation is the use of forward stimulation to modify connection weights, and is sometimes done to train the network using known correct outputs.

The systems and methods of the disclosure may use convolutional neural networks (CNN). A CNN is a feedforward network comprising multiple layers to infer an output from an input. CNNs are used to aggregate local information to provide a global predication. CNNs use multiple convolutional sheets from which the network learns and extracts feature maps using filters between the input and output layers. The layers in a CNN connect at only specific locations with a previous layer. Not all neurons in a CNN connect. CNNs may comprise pooling layers that scale down or reduce the dimensionality of features. CNNs hierarchically deconstruct data into general, low-level cues, which are aggregated to form higher-order relationships to identify features of interest. CNNs predictive utility is in learning repetitive features that occur throughout a data set.

The systems and methods of the disclosure may use fully convolutional networks (FCN). In contrast to CNNs, FCNs can learn representations locally within a data set, and therefore, can detect features that may occur sparsely within a data set.

The systems and methods of the disclosure may use recurrent neural networks (RNN). RNNs have an advantage over CNNs and FCNs in that they can store and learn from inputs over multiple time periods and process the inputs sequentially.

The systems and methods of the disclosure may use generative adversarial networks (GAN), which find particular application in training neural networks. One network is fed training exemplars from which it produces synthetic data. The second network evaluates the agreement between the synthetic data and the original data. This allows GANs to improve the prediction model of the second network.

The outcome data may include information related to a disease or condition. For example and without limitation, the outcome data may include information on one or more of tumor metastasis, tumor growth, or patient survival related to cancer. The cancer may be breast cancer, lung cancer, ovarian cancer, uterine cancer, cervical cancer, and vaginal cancer. The outcome data is from one or more individuals from whom other data, e.g., tissue images have been or will be entered into the machine learning system. In various embodiments the training sets may include image data from patients that are cancer free and the machine learning system may identify features that differentiate between cancer positive and cancer free tissues.

The features detected by the machine learning system may be any quantity, structure, pattern, or other element that can be measured from the training data. Features may be unrecognizable to the human eye. Features may be created autonomously by the machine learning system. Alternatively, features may be created with user input.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein.

The subject matter herein contains important information, exemplification and guidance that can be adapted to the practice of this invention in its various embodiments and equivalents thereof.

What is claimed is:

1. A method for assessing cancer risk, the method comprising:
   training a first image classifier to correlate biomarker data from tissue samples to features in images of the tissue samples using a first set of training data;
   providing an image of a tissue sample from a subject to the first image classifier;
   analyzing the image using the first image classifier to generate a first cancer risk score;
   training at least a second image classifier to correlate biomarker data from tissue samples to features in images of the tissue samples using at least a second set of training data;
   wherein if the first cancer risk score does not surpass a threshold, analyzing the image using the at least second image classifier to generate at least a second cancer risk score; and
   classifying a level of cancer risk for the subject using the first and at least second cancer risk scores.

2. The method of claim 1, wherein:
   the first set of training data comprises biomarker data and tissue sample images correlated with a cancer risk between a high and low cancer risk; and
   the second set of training data consists of biomarker data and tissue sample images correlated with at least a high and/or low cancer risk.

3. The method of claim 2, wherein the first set of training data further comprises biomarker data and tissue sample images correlated with a high and/or low cancer risk.

4. The method of claim 2, wherein the threshold is surpassed when the first cancer risk score indicates a high or low cancer risk.

5. The method of claim 4, wherein the method further comprises:
   training one or more additional image classifiers to correlate biomarker data from tissue samples to features in images of the tissue samples using at least a different set of training data for each classifier; and
   wherein if the first cancer risk score does not surpass a threshold, analyzing the image using the additional image classifiers to generate additional cancer risk scores.

6. The method of claim 5, wherein classifying includes using the first, second, and additional cancer risk scores.

7. The method of claim 4, wherein the cancer risk scores are assigned to a group, wherein each group corresponds to a different range of cancer risk scores.

8. The method of claim 7, wherein the second set of training data consists of biomarker data and tissue sample images correlated with a cancer risk score within the cancer risk score range of one or more selected group.

9. The method of claim 8, wherein the selected groups consist of a group with a highest range of cancer risk scores and a group with a lowest range of cancer risk scores.

10. The method of claim 7, wherein the method further comprises:
    training one or more additional image classifiers to correlate biomarker data from tissue samples to features in images of the tissue samples using at least a different set of training data for each classifier; and
    wherein if the first cancer risk score does not surpass a threshold, analyzing the image using the additional image classifiers to provide additional cancer risk scores.

11. The method of claim 10, wherein classifying includes using the first, second, and additional cancer risk scores.

12. The method of claim 11, wherein each of the second and additional classifiers are each trained using a different data set, and each different data set consists of biomarker data and tissue sample images correlated with a cancer risk score falling within the cancer risk score range of a different group.

13. The method of claim 11, wherein there are five groups, and the groups consist of:
    a first group with a range cancer risk scores correlated with an ultra-high risk of cancer;
    a second group with a range of cancer risk scores correlated with a high risk of cancer;
    a third group with a range of cancer risk scores correlated with an ambiguous risk of cancer;
    a fourth group with a range of cancer risk scores correlated with a low risk of cancer; and
    a fifth group with a range of cancer risk scores correlated with an ultra-low risk of cancer.

14. The method of claim 13, wherein if the first cancer risk score falls within the range of the third group, the first cancer score does not surpass the threshold.

15. The method of claim 14, wherein each of the second and additional classifiers are each trained using a different data set, and each different data set consists of biomarker data and tissue sample images correlated with a cancer risk score falling within the first, second, third, fourth, or fifth group.

16. The method of claim 15, wherein training the second and additional classifiers further includes:
    dividing each of the groups into at least two subdivisions, each subdivision corresponding to a different range of cancer risk scores; and
    training each of the second and additional classifiers using biomarker data and tissue sample images correlated with a cancer risk score within one or more of the subdivisions.

17. The method of claim 1, further comprising:
    segmenting the tissue image from the subject into segments;
    providing the segments to the image classifiers for analysis to generate cancer risk scores; and
    classifying a level of cancer risk for the subject using the generated cancer risk scores for each segment.

18. The method of claim 1, wherein the biomarker data comprises genomic data and/or RNA expression data.

19. The method of claim 18, wherein RNA expression data comprises RNA expression levels determined using sequencing or microarray analysis.

20. The method of claim 19, wherein RNA expression levels are determined by interrogating a sample with probes specific for a panel of genes and measuring expression levels for positive probe responses.

21. A method for assessing cancer risk, the method comprising:
    providing an image of a tissue sample from a patient to an image classifier trained on a plurality of tissue images, each associated with a cancer risk score;
    operating the image classifier on the image to output a risk score for the patient;
    when the risk score is within a range of threshold values between high-risk and low-risk scores, providing the image or the tissue sample to a second classifier that has been trained on tissue images, genomic characteristics, phenotypic characteristics or biomarker characteristics to obtain a second risk score for the patient.

22. The method of claim 21, wherein the cancer risk scores associated with the plurality of tissue images are divided into groups that include at least a highest risk group, a middle group for the range of threshold values between high-risk and low-risk scores, and a lowest risk group.

23. The method of claim 22, wherein the selected subset of the plurality of tissue images does not include any images associated with scores in the middle group.

24. A method for assessing cancer risk, the method comprising:
provid ing an image of a tissue sample from a patient to an image classifier trained on a plurality of tissue images, each associated with a cancer risk score;
operating the image classifier on the image to output a risk score for the patient;
when the risk score is within a range of threshold values between high-risk and low-risk scores, providing the image to a second classifier that has been trained using a selected subset of the plurality of tissue images to obtain a second risk score for the patient.

25. The method of claim 24, wherein the image classifier is trained by CLustering-constrained Attention Multiple instance (CLAM) learning.

26. The method of claim 24, wherein the image is a digital whole-slide image (WSI) of a stained section of tissue on a slide.

27. The method of claim 26, wherein the section includes tumor tissue and healthy stroma from the patient.

28. The method of claim 24, wherein the cancer risk score associated with each of the plurality of tissue images was obtained by genomic analysis for expression of a panel of genes.

29. The method of claim 28, wherein the genomic analysis is selected from arrays, next generation sequence, PCR, RNAseq, and hybrid capture.

30. The method of claim 24, wherein the second classifier has been trained by including only those images of the plurality of tissue images associated with a very high or very low risk score.

31. The method of claim 24, wherein the image classifier operates using a neural network or random forest.

32. The method of claim 24, wherein the image classifier divides the image into segments, scores each segment, identifies highest- and lowest-scoring segments, and calibrates scores for remaining segments based on the highest- and lowest-scoring segments.

33. The method of claim 24, wherein the cancer risk scores associated with the plurality of tissue images are divided into a number of groups such that a cutoff value between a positive and a negative cancer risk score lies within one group and not an a boundary between two groups.

34. The method of claim 33, wherein the selected subset of the plurality of tissue images does not include any images associated with scores in the one group.

35. The method of claim 24, further comprising pre-processing the image before operating the image classifier to select and include regions containing only certain tissue types.

36. The method of claim 35, wherein the image classifier computes an attention map for the included regions.

37. The method of claim 24, wherein the image classifier is trained on a plurality of tissue images that includes at least ten thousand images.

* * * * *